United States Patent
Altebaeumer et al.

(10) Patent No.: US 10,172,557 B2
(45) Date of Patent: Jan. 8, 2019

(54) WEARABLE BIOMETRIC DEVICE AND METHOD OF PERFORMING BIOMETRIC MEASUREMENTS

(71) Applicant: Dialog Semiconductor (UK) Limited, London (GB)

(72) Inventors: Thomas Altebaeumer, Green Park Reading (GB); Horst Knoedgen, Germering (DE)

(73) Assignee: DIALOG SEMICONDUCTOR (UK) LIMITED, London (GB)

( * ) Notice: Subject to any disclaimer, the term of this patent is extended or adjusted under 35 U.S.C. 154(b) by 342 days.

(21) Appl. No.: 15/249,259

(22) Filed: Aug. 26, 2016

(65) Prior Publication Data
US 2017/0055907 A1   Mar. 2, 2017

(30) Foreign Application Priority Data
Aug. 26, 2015   (DE) .......................... 10 2015 216 341

(51) Int. Cl.
*A61B 5/00*  (2006.01)
*A61B 5/1455*  (2006.01)
*A61B 5/024*  (2006.01)

(52) U.S. Cl.
CPC ........ *A61B 5/6843* (2013.01); *A61B 5/02416* (2013.01); *A61B 5/1455* (2013.01); *A61B 5/14551* (2013.01); *A61B 5/681* (2013.01); *A61B 5/6844* (2013.01); *A61B 2560/0209* (2013.01); *A61B 2560/0233* (2013.01); *A61B 2562/029* (2013.01); *A61B 2562/0219* (2013.01); *A61B 2562/0233* (2013.01)

(58) Field of Classification Search
CPC .............. A61B 5/02416; A61B 5/1455; A61B 5/14551; A61B 5/681; A61B 5/6843; A61B 5/6844; A61B 2560/0209; A61B 2560/0233; A61B 2562/0219; A61B 2562/0233; A61B 2562/029
USPC ................................................... 600/300, 301
See application file for complete search history.

(56) References Cited

U.S. PATENT DOCUMENTS

| 2015/0124566 A1* | 5/2015 | Lake | ...................... G04G 21/08 368/10 |
| 2015/0135310 A1* | 5/2015 | Lee | ........................ A61B 5/681 726/20 |

(Continued)

FOREIGN PATENT DOCUMENTS

| DE | 43 29 898 A1 | 4/1995 |
| WO | WO 2009/086576 A1 | 7/2009 |

*Primary Examiner* — Michael Carey
(74) *Attorney, Agent, or Firm* — Haynes and Boone, LLP

(57) ABSTRACT

A wearable biometric device includes a biometric sensor system adapted to measure a predetermined physiological property of a user's body at two or more different locations at the body surface and to provide for each such location an associated primary signal indicative of said measured physiological property. The device also includes a detector system adapted to detect a level of coupling of the biometric sensor system with the body at each of the locations and to provide for each of the locations an associated secondary signal indicative of said detected level of coupling and also includes a signal processing unit adapted to generate an output signal indicative of said physiological property as a function of the primary and secondary signals.

20 Claims, 5 Drawing Sheets

(56) References Cited

U.S. PATENT DOCUMENTS

2016/0199002 A1\* 7/2016 Lee ................... A61B 5/0008
340/870.07
2016/0367158 A1\* 12/2016 Samadani ............. A61B 5/721

\* cited by examiner

WEARABLE BIOMETRIC DEVICE AND METHOD OF PERFORMING BIOMETRIC MEASUREMENTS

CROSS REFERENCE TO RELATED APPLICATIONS

This application claims priority to German patent application no. 10 2015 216 341.5, filed Aug. 26, 2015.

FIELD OF THE INVENTION

The present invention relates to the field of wearable electronic devices having sensors to measure biometric properties of the human body, in particular properties of the blood's composition and its flow through the body. Specifically, the invention is directed to a wearable biometric device and a method of performing biometric measurements at such a device.

BACKGROUND

With the ongoing miniaturization of electrical components and portable electronic devices in the last few years a new product category of so-called "wearables" has emerged, which comprises wearable wireless electronic devices with sensors for measuring biometric properties of a person wearing such a device. Fitness bands (e.g. fitness bands by fitbit Inc. of San Francisco, Calif., electronic watches (e.g. the Apple Watch by Apple Inc. of Cupertino, Calif.) and wearable wireless medical devices are examples of such wearables with biometric sensors.

In particular, some of these known devices are equipped with one or more sensors for measuring the composition and/or flow of blood in the body of the person wearing the device. The measurement of the composition of blood might for example relate to a measurement of levels of oxygen, nutrients or metabolic waste products in the blood. Measurements of the flow of blood might for example relate to the pulse at which the blood is pumped by the heart through the body. One way of performing such measurements is by using optical means provided within the wearable device, wherein a light source (such as an LED) is used to emit a beam of radiation, in particular light in the visible or infrared part of the electromagnetic spectrum, towards and under the skin of the person. An optical sensor (such as a photodiode) is then used to detect the radiation reflected from the body, in particular from blood flowing in the blood vessels below the skin. The spectral response of the detected reflected radiation can be analyzed in order to derive the biochemical composition of the blood, because the various types of molecules to be detected within the composition of the blood have specific individual spectral responses to the radiation emitted by the light source. Therefore, the optical sensor has to be able to distinguish different wavelengths of the spectrum. To achieve this, filters can be used, in particular narrow filters with a bandwidth of about 50 nm or less. In order to detect the flow of blood, esp. its pulse, variations over time of the pulse-dependent intensity of the detected responses can be measured. In particular, the intensity is dependent on the oxygen level in the blood and thus serves as a good indicator for the pulse, as the oxygen content of blood at a particular vessel location usually varies, at least roughly, with the rhythm of the pulse.

Many wearable devices with biometric sensors, in particular if they are designed as watches or fitness bands, are worn at an extremity of the body, mostly at the wrist, and may have a bracelet to fix them thereto. While pulling the bracelet rather tight enables a higher quality of measurement, because then one or both of the lateral position and the distance of the sensor relative to the skin are less likely to change when the body moves, this is often considered very inconvenient for the person wearing the device. Thus, despite their intended biometric functionality, such wearable devices are often worn rather loosely thus reducing measurement quality or even preventing of meaningful measurements. This in turn might lead to a reduction of acceptance of such devices by users and ultimately to a reduced use rate or even a termination of use. Similar problems can also occur, when the wearable device is not to be worn at the wrist but is designed to be in some other way coupled to the body, e.g. at other parts of the extremities or around the chest (e.g. by a chest strap).

In the field of wired medical devices, in particular oximeters, it is known to use several sensors and to switch between them to manually or automatically and even dynamically select only one of the various measured sensor outputs as input signal to the medical device.

Such a solution is known from U.S. Pat. No. 6,510,331 to Williams et al., which discloses a switching device being interposed between a conventional oximeter and a plurality of conventional photo sensors. Photo sensors are located on different extremities of the body. The switching device may be operated in a manual mode or an automatic mode. In the manual mode, each different photo sensor may be individually selected to provide the input signal to the oximeter. In the automatic mode, the switching device scans the incoming signals from the different photo sensors and forwards the best, strongest or least distorted signal to the oximeter. The device prevents the loss of oximetry information due to interrupted blood flow in a particular part of the body or the failure of a sensor.

SUMMARY OF THE INVENTION

It is an object of the present invention to provide an improved solution for the measurement of biometric properties of the human body at or near the body surface, in particular properties of the blood's composition and its flow through the body, by a wearable biometric device.

A solution to this problem is provided by the teaching of the independent claims, specifically by a wearable biometric device according to claim 1, and by a method of performing biometric measurements at a wearable biometric device according to claim 16.

Various preferred embodiments of the present invention are provided by the teachings of the dependent claims.

A first aspect of the invention is directed to a wearable biometric device. The device comprises a biometric sensor system adapted to measure a predetermined physiological property of a user's body in relation to two or more different locations at the body surface and to provide for each such location an associated primary signal indicative of said measured physiological property. Furthermore, the device comprises a detector system adapted to detect a level of coupling of the biometric sensor system with the body at each of the locations and to provide for each of the locations an associated secondary signal indicative of said detected level of coupling. In addition, the device comprises a signal processing unit adapted to receive the primary signals and the associated secondary signals, and to generate an output signal indicative of said physiological property as a function of the received primary and secondary signals, such that the output signal's functional dependency on a first one of the primary signals is less than its functional dependency on a second one of the primary signals, if the secondary signal associated with the first one of the primary signals indicates a lower coupling level than the secondary signal associated with the second one of the primary signals.

The term "wearable biometric device" in the sense of the present invention refers to a portable electronic device having sensors for measuring biometric properties of a person wearing such a device. In particular, the device may be equipped with means to fasten or otherwise attach it to the body of the person. Those means may in particular comprise one or more straps, bands, bracelets, tapes, Velcro® tapes etc. Specifically, in some embodiments the device may have the form factor of a wrist band or a watch or a chest strap.

The term "biometric sensor system" in the sense of the present invention refers to a system comprising two or more biometric sensors for measuring one or more specific physiological properties of a user's body. The biometric sensors are arranged in relation to two or more different locations at the body surface, such that the sensor can measure a respective physiological property of the user's body as it is detectable at such a respective location. Without limitation, a biometric sensor may be arranged directly at and in contact with the user's body at a respective location, or it may be arranged at a distance therefrom and take measurements via one or more physical entities connecting the biometric sensor to the location, e.g. electromagnetic radiation (such as visible or infrared light), air (pressure, humidity, acoustic wave) etc. While typically the user will be a human person, it is equally possible that the user is an animal, in particular a mammal, showing such physiological property. The sensors are arranged such that they can be located at two different distinct positions of the user's body, in particular its skin, in order to individually perform measurements of said specific one or more physiological properties. Each of the sensors can provide a primary signal indicative of said one or more physiological properties as measured by that sensor. Specifically, if the biometric property is the pulse of blood, then the primary signal may relate to or be derived from the pulse rate detected by the sensor at its location.

The term "detector system" in the sense of the present invention refers to a system comprising one or more detector devices adapted to detect a level of coupling of the biometric sensor system with the body at two or more locations, specifically at the locations of the biometric sensors of the biometric sensor system. The detector system is adapted to provide for each of the locations an associated secondary signal indicative of said detected level of coupling.

The term "level of coupling" in the sense of the present invention refers to a parameter defining the quality of coupling of the detector system to a user's body. It may thus provide an indication for the quality of measurement that can be achieved with a biometric sensor positioned at or in the close vicinity of one of the locations. The level of coupling may in particular refer to a spatial distance, preferably the shortest distance, between the detector system and the body, or the strength of a signal detected by the detector system. The strength of the signal may be defined in absolute terms or relative to some gauge signal, e.g. a predetermined signal corresponding to a measurement at ideal coupling conditions.

The term "signal processing unit" in the sense of the present invention refers to an entity that is capable of receiving one or more input signals, e.g. analog or digital signals, in electronic or optical or any other suitable form, and to process them, e.g. by application of one or more algorithms or filtering or any other method, in order to generate one or more output signals. The signal processing unit may be implemented in hardware or software or a mix of both. Specifically, both hardwired electronic signal processing circuits with fixed functionality and programmable microprocessors, such as digital signal processors (DSP), the function of which depends on their programming, are signal processing units in the sense of the present invention. Particularly, a signal processing unit may comprise one or more processing cores. In the sense of the present invention "the output signal of the signal processing unit is indicative of said physiological property as a function of the received primary and secondary signals", if the output signal is one of the primary signals or is derived therefrom or from multiple primary signals, wherein the selection or derivation of the output signal from the primary signals is based on the received one or more secondary signals. Thus, one or more of the secondary signals determine how the output signal is selected or derived from the set of two or more primary signals.

The term "functional dependency" in the sense of the present invention refers to the relationship between a predetermined quantity associated with the output signal and a predetermined quantity associated with a particular one of the primary signals. In particular, the quantity associated with a signal may be its amplitude, its frequency, its phase or some other physical property of the signal, or a quantity carried by the signal as data. The functional dependency of the output signal from a primary signal quantifies the change of the quantity associated with the output signal caused by a specific change of the quantity associated with that particular primary signal. Accordingly, the output signal's functional dependency on a first one of the primary signals is less than its dependency on a second one of the primary signals, if the change of the quantity associated with the output signal for a given change of the quantity associated with the first one of the primary signals at a given starting point, i.e. for a given set of values of all primary signals, is smaller than the change in value of the output signal for the same change of the respective quantity associated with the second one of the primary signals. Preferably, the output's functional dependency or at least the validity of this inequality ("less than") is independent from a specific starting point. Specifically, for differentiable functional relationships (dependencies), the functional dependency may be defined as a derivative of the quantity associated with the output signal with respect to the quantity associated with a respective one of the primary signals.

Accordingly, the output signal indicative of said physiological property can be generated from the primary signals based on the detected secondary signals and thus depending on the level of coupling of the various sensors to the body, which in turn is indicative of the quality of measurement at the individual sensors. Thus the reliability of the output signal is improved and the above underlying problem is solved. Furthermore, the sensor system does not have to be fixed as strongly to the body as conventional systems in order to achieve a sufficient overall measurement quality. Thus the comfort of wearing such a wearable biometric device while maintaining its ability to provide reliable biometric measurement results can be significantly increased.

In the following, preferred embodiments of the wearable biometric device are described, which can be arbitrarily combined with each other or with other aspects of the present invention, unless such combination is explicitly excluded or technically impossible.

According to a first preferred embodiment, in an active mode the energy consumption of the detector system per location is lower than that of the biometric sensor system, and the signal processing unit is further adapted to selectively activate the biometric sensor system such that the generation of a respective primary signal is activated only for one or more selected locations having a coupling level, as indicated by the associated secondary signals, above a defined threshold. Thus, instead of an "always-on" operation of the biometric sensor system it becomes possible to only operate the detector system continuously, while the biometric sensor system, e.g. its individual biometric sensors, is merely activated selectively when and where actually needed. In this way, as the power consumption of the detector system per location is lower, the overall power consumption can be reduced. In particular, it is also possible to only activate a single one of the biometric sensors at a time, in particular the one with the best coupling as indicated by its corresponding secondary signal, such that the power consumption can be minimized while maintaining an acceptable or even optimized measurement quality. A further advantage might be achieved in view of measurement speed, because weak levels of coupling of the biometric sensors to the body usually cause reduced measurement speeds, i.e. delays, due to signal distortions or losses and thus interruptions or repetitions of the measurements before a reliable measurement value can be detected. If, however, only one or more biometric sensors having a sufficiently good coupling as indicated by the related secondary signals are activated, such speed reductions respectively delays can be effectively avoided and the primary signals and eventually the output signal can be provided faster.

According to another, related preferred embodiment, which may particularly be combined with the preceding one, the signal processing unit is further configured to initiate a transition of the biometric sensor system into a low power mode, which may preferably involve deactivating the biometric sensing, when for a predetermined duration no secondary signals indicating a sufficiently good level of coupling have been received. Thus power for measuring may be saved, when no meaningful measurements are possible. In particular, according to a preferred variant of this embodiment, in which the biometric sensor system comprises at least one radiation source arranged to emit electromagnetic radiation, transitioning into the low power mode involves reducing the intensity or duration of emission of such radiation or, preferably, deactivating such emission. In addition to a benefit of power saving, if the radiation emitted by the radiation source is potentially harmful to other parts of a user's body (such as his eyes) or its environment, transitioning into the low power mode and reducing or deactivating emission, when the coupling level is insufficient such as when the device is no longer worn by the user, can increase the safety of use of the wearable biometric device.

According to another preferred embodiment, the biometric sensor system is operable in different modes of operation including a first mode in which it is configured to provide said primary signals, and a second mode, in which it is configured to provide at least a subset of said secondary signals. Thus, the detector system may be implemented, at least partially, by reusing the biometric sensor system, such that the number of separate detectors for generating the secondary signals can be reduced or such detectors can even become obsolete. In particular, the biometric sensors might be operable in a time division mode, where phases of operating the biometric sensor system or one or more individual biometric sensors thereof in the first mode alternate with phases of operating the biometric sensor system respectively the one or more individual biometric sensors thereof in the second mode of operation. This may also be done group wise, such that at a given point in time one or more first subsets of the biometric sensors are operable in the first mode of operation while at the same time one or more other subsets of the biometric sensors are operable in the second mode of operation. In particular, in the second mode of operation at least one of the biometric sensors may be operable to generate the secondary signal based on the signal-to-noise ratio and/or another coupling dependent property of the primary signal.

According to another preferred embodiment, the signal processing unit is further adapted to selectively receive the primary signals, the secondary signals, or both as a function of time or the associated locations, or both. Thus, for example a clocked reception might be implemented, wherein measurement and thus related power consumption is temporarily paused, in particular periodically, before it is resumed. The signal processing unit may also be configured to at least temporarily (e.g. in a power saving mode) only receive and process primary and secondary signals from selected locations among all locations, in order to reduce the number of signals to be received and processed and thus the related power consumption.

According to another preferred embodiment said function of the received primary and secondary signals to be used by the signal processing unit for generating the output signal involves forming a weighted sum of the received primary signals, wherein the weight of a first one of the primary signals is smaller than the weight of a second one of the primary signals, if the secondary signal associated with the first one of the primary signals indicates a lower coupling level than the secondary signal associated with the second one of the primary signals.

In particular, the function and thus the output signal's functional dependency on the primary signals might be defined as a weighted average, wherein the quantity $S_O$ associated with the output signal is defined as a weighted sum of the quantities $Sp_i$ associated with the N respective primary signals and wherein the respective weight $w_i$ associated with the $i^{th}$ primary signal is proportional or equal to the level of coupling indicated by the corresponding secondary signal. In particular $S_O$ may be defined as follows:

$$S_O = \frac{\sum_{i=1}^{N} w_i \cdot Sp_i}{\sum_{i=1}^{N} w_i}$$

Thus, the individual primary signals only contribute to the output signal according to their weight, which in turn depends on the respective level of coupling. As a consequence, distortions of the output signal by insufficient or weak coupling levels are reduced, while a robust determination of the output signal based on multiple different primary signals is maintained, such that measurement errors related to individual biometric sensors can be averaged out. Furthermore, the weights $w_i$ might be chosen such that only a subset of one or more of the weights have a value different from zero. Preferably, those one or more weights correspond to secondary signals indicating an above-average level of coupling. In particular, only the weight respectively weights of a subset of one or more primary signals having corresponding secondary signals indicating the highest relative levels of coupling among all secondary signals are different from zero. Thus only the primary signals corresponding to sensors that show the relative (i.e. not necessarily absolute) best level of coupling, are contributing to the determination of the output signal.

According to another preferred embodiment the detector system comprises one or more distance sensors configured to measure the respective distances between each of at least two of said locations at the user's body and the biometric sensor system. Thus, the level of coupling can be easily determined based on a simple distance measurement. In it simplest case, the distance measurement is a mere binary contact measurement that determines, whether the detector system is in contact with the body at the respective location or not. Beyond simplicity, another advantage of using distance measurement for determining the coupling level is the fact that the distance is frequently a key factor of influence for the quality of a biometric measurement to be performed by a co-located biometric sensor of the biometric sensor system.

According to another preferred embodiment the detector system comprises at least one light source adapted to emit a predetermined calibration light signal (preferably in the visible or infrared part of the spectrum) towards the user's body when the device is worn by the user. The detector system further comprises at least one light detector adapted to receive the light signal after it has been reflected at a location on the user's body and to generate a secondary signal corresponding to the level of coupling at the location based on a comparison of the received reflected signal with the predetermined calibration signal. Thus, effective detection of a level of coupling is enabled that does not depend on a physical contact of the detector to the body, i.e. the skin. In fact, this detection also works if there is a gap between the detector and the skin at the location. According to a preferred variant, the detector system is operable in one mode to have the light detector detect light received while the light source is not active in order to determine a base signal related to light received from the environment and to determine the calibration signal based thereon.

According to another preferred embodiment the biometric sensor system comprises at least one radiation source, such as a LED. The source is arranged to emit electromagnetic radiation, at least partially, onto one or more of said locations at the user's body when the biometric device is worn by the user. In particular, the radiation may be light in the visible or infrared part of the electromagnetic spectrum. The biometric sensor system further comprises at least one corresponding radiation sensor adapted to receive said radiation, at least partially, after it has passed through or has been reflected by the body. Furthermore, the biometric sensor system comprises one or more waveguides for directing the radiation from the at least one radiation source to one or more of the locations or from there to the at least one corresponding radiation sensor, or both. Thus, the positions of the radiation source and/or the one or more radiation sensors can be spatially decoupled from the locations on the body where the measurements are made. Furthermore, it is possible to form the waveguides such that the radiation is split such that it propagates along two or more different radiation paths at once, so that the number of radiation sources respectively radiations sensors can be less than the number of locations. In particular, this provides an efficient way of limiting the number of radiation sources and/or radiation sensors to only one of each. The use of waveguides also allows for transferring the signals within the biometric sensor system without adding electromagnetic noise. Preferably, the waveguides are made from a glass or plastic material being transparent for the radiation emitted by the at least one source of radiation, at least in the wavelength range used of the measurements. At least one of the waveguides may be formed as a fiber, i.e. may be a fiber optical waveguide.

According to a first preferred variant of this embodiment the biometric sensor system further comprises an optical switch adapted to selectively direct radiation emitted by the at least one radiation source to a subset of one or more of the locations. In particular, the optical switch may comprise one or more mirrors. Preferably the individual mirrors can be positioned, particularly tilted, such that the radiation reflected by the mirror is directed into one or more particular selected radiation paths defined by the one or more waveguides and leading to corresponding locations. Thus, it is possible to direct the radiation only to a subset of one or more selected ones of the locations where a measurement is to be performed. Preferably, these are locations for which the coupling level as indicated by the respective secondary signals is higher than for the non-selected locations. As a consequence, the radiation power of the one or more radiation sources can be reduced, because it is not necessary to guide radiation to all locations. If, for example, only two out of eight locations are selected, then no radiation has to be generated for and guided to the six non-selected locations and accordingly the radiation power can be reduced, e.g. to approximately to a quarter of the power being necessary to provide an adequate level of radiation to all of the eight locations.

According to another preferred variant of this embodiment, which may also be combined with the first variant above, the biometric sensor system further comprises a shutter system for selectively blocking one or more radiation paths provided in the one or more waveguides, the paths connecting the locations to corresponding one or more radiation sensors. The shutter system may particularly comprise one or more liquid crystal display elements (LCD) operable to switch between at least two modes of different transparency to the radiation and being controlled e.g. by applying a respective voltage. The shutter system allows for a selection of radiation paths between the various locations and the one or more radiation sensors, such that only radiation propagating along such selected paths reaches the one or more radiation sensors in order to be detected there. In particular, if the shutter system is used in connection with the optical switch of the first variant, there are effectively two independent selection means in the biometric sensor system. Then, the optical switch may particularly be used as a first selector to only provide radiation to those locations where, preferably according to the corresponding coupling level as indicated by the respective secondary signals, measurements shall be made. The shutter system may then be used to scan those selected locations, e.g. serially similar to a time division multiplexing scheme, to open a radiation path between one or more currently scanned locations on the one hand and one or more radiation sensors on the other hand. Thus the number of locations may be higher than the number of radiation sensors, while still separate measurements with respect to the various biometric sensors remain possible. This may be advantageous, as it allows using a reduced number of biometric sensors, which in turn may reduce spatial requirements, i.e. size, cost, weight, and/or complexity of the biometric sensor system and the wearable biometric device as a whole.

According to another preferred variant of this embodiment the at least one radiation source is adapted to selectively emit radiation in different predetermined wavelengths or wavelength ranges that are aligned with the spectral responses of corresponding different chemical substances to be detected within the user's body. Thus, it is possible to distinctly limit the measurements taken by the biometric sensor system to specific selectable chemical substances. This may be used in different ways, particularly for optimizing the reliability and/or accuracy of the system, if specific chemical substances are better indicators for quantities to be measured at the body, or for selectively measuring specific biometric properties related specifically to those selected chemical substances, like for example metabolic waste products.

According to another preferred embodiment, which may in particular be used instead or in addition to the selective emission of radiation of the immediately preceding embodiment, the biometric sensor system comprises at least one radiation source arranged to emit electromagnetic radiation, at least partially, onto one or more of said locations at the user's body when the biometric device is worn by the user. Furthermore, the system comprises at least one corresponding radiation sensor to receive said radiation, at least partially, after it has passed through or has been reflected by the body, and a filter arrangement. The filter arrangement comprises one or more radiation filters arranged between one or more of the radiation sources on the one hand and corresponding one or more of the radiation sensors on the other hand. It is configured to selectively let pass radiation in one or more passing band regions of the wavelength spectrum emitted by the one or more radiation sources, wherein the passing band regions correspond to wavelength ranges of the spectral responses of preselected chemical substances to be detected. According to a preferred variant, at least one of the radiation filters is located at a respective radiation sensor. In particular, it may be formed as part of the respective radiation sensor. Preferably, the bandwidth of at least one pass band region is 15 nm or even less, in order to provide for a precise identification of substances showing characteristic narrow emission peaks in their spectrum.

According to another preferred embodiment the biometric sensor system comprises, like in the previous embodiment, at least one radiation source arranged to emit electromagnetic radiation, at least partially, onto one or more of said locations at the user's body when the biometric device is worn by the user, and at least one corresponding radiation sensor to receive said radiation, at least partially, after it has passed through or has been reflected by the body. At least one of the radiation sensors comprises two or more photodiodes arranged in different layers of a stack. The stack has a top face configured to receive radiation to be detected and each photodiode has one or more specific sensitivity wavelength ranges in which it can detect radiation. One or more of the photodiodes are organic photo diodes being at least partially transparent to radiation having a wavelength outside of their respective one or more sensitivity wavelength ranges and a first one of the one or more organic photodiodes is arranged in a first layer positioned closer to the top face of the stack than a second layer comprising a second one of the photodiodes such that at least a portion of incoming radiation to be detected first reaches the first organic photo diode before reaching the second photodiode. Preferably, according to a preferred variant of this embodiment, one or more of the layers are only transparent for components of the radiation outside the sensitivity wavelength range of their respective one or more photodiodes. Thus the layers may also act as wavelength filters. Particularly, the corresponding absorption spectrum—corresponding to the one or more sensitivity wavelength ranges—of a first layer positioned closer to the top surface of the stack than a second layer may be narrower than the absorption spectrum of the second layer. Specifically, the layers are preferably ordered from the top-surface to the bottom of the stack according to the width of the absorption spectrum from narrow towards broad. Preferably, the absorption spectra of the different layers do not overlap.

In addition to one or more organic photo diodes, the radiation sensor may comprise one or more inorganic photo diodes, such as Si-based photodiodes. Each inorganic photodiode is then typically arranged in a layer of the stack located below one or more organic photodiodes within the stack, such that incoming radiation to be detected first passes through the one or more organic photodiode layers before reaching the inorganic photo-diode. In particular, the Si-based photodiode may form all or a part of an integrated circuit, such as a CMOS-circuit. If there are more than one inorganic photodiodes, they may be particularly arranged laterally next to each other within the same layer of the stack.

Advantages of this embodiment may comprise that the space efficiency of the radiation sensor arrangement can be increased, because different photodiodes for different wavelength ranges can be arranged on top of each other on the same footprint. Each of the organic photodiodes selectively absorbs essentially only those photons of the radiation, which pertain to the respective wavelengths respectively photon energies to which the respective radiation sensor is sensitive, while photons of other wavelengths within a respective pass band can pass towards the next layer of the stack.

According to another preferred embodiment the biometric sensor system comprises one or more of the following types of sensors: oximeter, temperature sensor, humidity sensor, accelerometer, radiation sensor. Particularly, an oximeter may be used to detect the concentration of oxygen in blood which may vary along with the pulse and thus the oximeter may also be used to detect the pulse. Temperature and humidity sensors allow for detecting body temperature respectively humidity on the skin of the body, which in turn might be used as indicators for various health or fitness aspects, such as for sensing the person's current level of activity or for detecting fever. Preferably, this may be done in connection with measurements of other quantities, such as pulse. An accelerometer may be used to detect motion or specifics thereof. Preferred uses of radiation sensors, such as optical sensors, have already been discussed above. According to a preferred variant, the biometric sensor system comprises biometric sensors of different kinds which are adapted to measure different physiological properties and generate respective primary signals.

According to another preferred embodiment the wearable biometric device further comprises a first temperature-sensitive electrical resistor arranged at a first position on a contact surface of the wearable biometric device, the contact surface being configured to get in contact with the user's body surface at a first location corresponding to the first position, when the wearable biometric device is worn by a user. The detector system is operable to cause a temporary flow of current through the first resistor that results in a temperature increase at the resistor, to determine a level of coupling of the biometric sensor system with the body based on a physical quantity affected by a change of the resistance of the first resistor caused by the temperature increase, and to provide an associated secondary signal indicative of said detected level of coupling. The physical quantity may particularly be a voltage drop across the resistor.

In the sense of the present invention a "temperature-sensitive resistor" is an electrical component that has at least one state of operation in which it conducts electricity and has electrical resistance that is temperature dependent. The dependency may be positive, i.e. the resistance increases when the temperature increases, or negative, i.e. the resistance decreases when the temperature increases. In particular, ohmic resistors, transistors, and diodes are temperature-sensitive resistors in the sense of the application. Preferably, the temperature-sensitive resistor has a linear temperature-coefficient a with an absolute amount $|\alpha|$ of at least $1*10^{-3}$ $K^{-1}$ at 20° C., thus yielding a strong temperature dependency of the resistance that can be easily detected.

Thus, when the first resistor gets in contact with the body and thus gets thermally coupled to it, a temperature increase caused by the temporary current will be lower than when the resistor is not in contact with the body, because a significant portion of the heat generated by the current in the resistor can dissipate away through the body when it is in contact with the resistor, while the surrounding air essentially acts a thermal isolator. Furthermore, the thermal coupling depends on the level of coupling between the resistor and thus the device's surface and the body. Accordingly, measuring said physical quantity, e.g. a voltage drop across the resistor during or shortly after the temperature increase, provides a measure for the level of coupling between the body and a biometric sensor co-located or located at least in the neighborhood of the resistor on said surface of the device. Further advantages comprise that such resistors may be implemented at low cost and with a very small footprint, such that a plurality of them may be placed on a contact surface of the biometric device in addition to biometric sensors, even the device's size is rather limited, for example when the size of the contact surface is only a few square centimeters.

According to a preferred variant of this embodiment the wearable biometric device further comprises a second electrical resistor arranged on the contact surface of the wearable biometric device at a second position being different from the first position, the contact surface being further configured to get in contact with the user's body surface at a second location corresponding to the second position, when the wearable biometric device is worn by a user. The biometric sensor system is operable to apply a voltage between the first and the second resistor to measure a physiological property of the body that affects the resistance of a current path forming between the first location and the second location across the body when both resistors are in contact with the body and the voltage is applied between the two resistors by measuring a physical quantity depending on said resistance of the current path, and to provide a primary signal associated with the first location or the second location that is derived from the measured quantity. Thus, the resistors may serve different purposes. On the one hand, they can be operated as distance sensors for determining a level of coupling at the respective first and second locations as indicated by corresponding secondary signals based thereon. On the other hand, they can be operated as sensors for physiological properties of the body, such as humidity on the skin, that affect the resistance of a current path between the two locations, as indicated by corresponding primary signals based thereon.

According to another preferred embodiment the biometric sensor system, the detector system or both are structured as a fixed array of individual sensors respectively detectors, and the signal processing unit is further adapted to derive from the primary or secondary signals or both on the one hand the positions of the sensors respectively detectors in the array and on the other hand a position of the wearable biometric device relative to the user's body, by applying a recognition algorithm to said signals. The signal processing unit is further adapted to determine said function of the received primary and secondary signals for generating the output signal based on one or more patterns on the user's body that were recognized by the application of said pattern recognition algorithm.

In particular, this can be advantageously used for selectively activating only those sensors of the biometric sensor system which according to the recognized pattern are best positioned relative to the body to perform their measurements or to at least assign to such primary signals a greater functional dependency of the output signals than to primary signals at other less preferred locations. In preferred variants, the pattern recognition algorithm is configured to recognize blood vessels (e.g. for pulse measurements) or a skin area with a low density of hair or dirt or other objects which might negatively affect the measurement reliability (e.g. for humidity measurements).

According to another preferred embodiment, the detector system or the signal processing unit are configured to generate a signal, e.g. a visual, acoustic or haptic signal, if during a predetermined duration, e.g. a few seconds or minutes, like for example 5 to 60 seconds, the coupling level of the biometric sensor system has been below a predetermined threshold level for all of the locations, wherein the threshold level defines a minimum level for meaningful measurements of the respective physiological property. In a preferred variant of this embodiment, the duration may be adapted to a previously detected activity level, as indicated for example by a detected blood pulse. In particular, the duration may be shorter during phases of detected activity, e.g. higher pulses than in phases of rest, e.g. when lower pulses had been detected. Thus the detection may be adapted to the activity level of the user and power (for generating an alarm) may be saved during phases of rest or low activity, e.g. during sleeping phases. Furthermore, during such low activity phases, in particular sleep phases, alarm signals might be considered disturbing. Accordingly, the generation of alarms may also be automatically disabled, when the detected activity level is below a certain predetermined threshold, e.g. pulse threshold, for a defined duration.

A second aspect of the present invention is directed to a method of performing biometric measurements at a wearable biometric device. The method comprises: measuring, with a biometric sensor system, a predetermined physiological property of a user's body in relation to two or more different locations at the body and generating for each such location an associated primary signal indicative of said measured physiological property;

detecting, with a detector system, a level of coupling of the biometric sensor system with the body at each of the locations and providing for each of the locations an associated secondary signal indicative of said detected level of coupling;

generating, an output signal indicative of said physiological property as a function of the primary and secondary signals, such that the output signal's functional dependency on a first one of the primary signals is less than its dependency on a second one of the primary signals, if the secondary signal associated with the first one of the primary signals indicates a lower coupling level than the secondary signal associated with the second one of the primary signals.

This method corresponds to the operation of the wearable biometric devices as already described in detail above in connection with the first aspect of the present invention. In particular, this method may also be used in connection with the various embodiments and variants of the device according to the first aspect as described above and respective method steps corresponding to the functionalities of the wearable biometric device as described in detail herein, may be added.

BRIEF DESCRIPTION OF THE DRAWINGS

Further advantages, features and applications of the present invention are provided in the following detailed description and the appended figures, wherein.

DETAILED DESCRIPTION OF PREFERRED EMBODIMENTS

Figure 1:
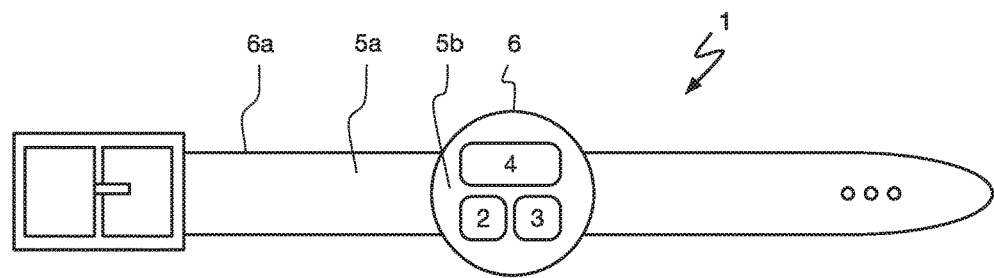
FIG. 1 schematically illustrates a wearable biometric device with sensors arranged in a housing, according to a preferred embodiment of the present invention.

FIG. 1 illustrates a wearable biometric device 1 designed as a wrist worn watch, according to a preferred embodiment of the present invention. The device 1 is shown from its rear side and comprises a housing 6 connected to a bracelet 6a for fixing the watch to the wrist of a user. The surface portions of the device 1 that are designed to get in contact with the skin of the user's body, i.e. at the wrist, define a contact surface with a first contact portion 5a on the rear side of the bracelet 6a and a second contact surface portion 5b at the rear side of the housing 6.

The second contact surface portion 5b of the housing 6 comprises a biometric sensor system 2 and a detector system 3, which are arranged such that when the second contact surface portion 5b is brought into contact with the skin of the user, the biometric sensor system 2 also gets in contact with it, at least at one location, and is thus enabled to perform at the location measurements of one or more physiological properties of the user's body and to provide for each such location and associated primary signal indicative of said measured physiological property.

The detector system 3 is adapted to measure a level of coupling between the second contact surface portion 5b and the user's body. In particular, the detector system is adapted to detect a level of coupling of the biometric sensor system with the body at each of the locations and to provide for each of the locations an associated secondary signal indicative of said detected level of coupling. For that purpose, the detector system 3 may in particular comprise one or more distance sensors for detecting a distance between the second contact surface portion 5b, in particular a sensor of the biometric sensor system 2, and the body at one or more locations.

Both, the biometric sensor system 2 and the detector system 3 are connected to a signal processing unit 4 provided within the housing 6. The signal processing unit 4 is adapted to receive the primary signals and the associated secondary signals and to generate an output signal indicative of said physiological property as a function of the received primary and secondary signals. The output signal's functional dependency on a first one of the primary signals is less than its functional dependency on a second one of the primary signals, if the secondary signal associated with the first one of the primary signals indicates a lower coupling level than the secondary signal associated with the second one of the primary signals.

Figure 2:
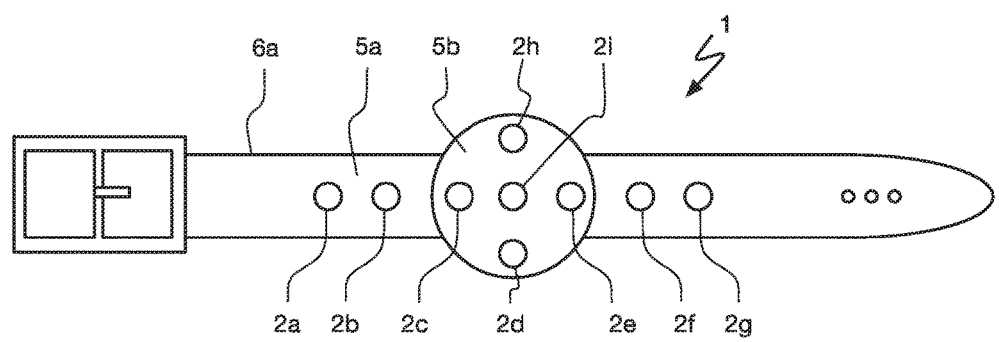
FIG. 2 schematically illustrates a wearable biometric device with sensors arranged both in a housing and on a bracelet, according to another preferred embodiment of the present invention.

FIG. 2 illustrates a wearable biometric device 1 designed as a wrist worn watch, according to another preferred embodiment of the present invention. This embodiment is identical to the embodiment of FIG. 1, except that the biometric sensor system 2 and the detector system 3 are now distributed on the contact surface portions 5a and 5b across both the housing 6 and the bracelet 6a. In particular, according to this embodiment, both the biometric sensor system 2 and the detector system 3 comprise various sensors respectively detectors arranged at different positions on the contact surface. Specifically, the individual sensors of the biometric sensor system and the individual detectors of the detector system are paired, such that at each of the positions, there is a combined sensor 2a to 2i comprising a biometric sensor and a detector. Those combined sensors 2a to 2i are arranged in a regular array extending across at least parts of the rear side of the bracelet 6a, i.e. the contact surface portion 5a, and the rear side of the housing 6, i.e. the contact surface portion 5b. Is an advantage of this embodiment that the effective size of the contact surface is extended beyond the rear surface of the housing 6 itself. Thus the probability of at least one of the combined sensors 2a to 2i having a sufficient level of coupling with the body for performing a reliable measurement of the respective physiological property, can be significantly increased.

Figure 3:
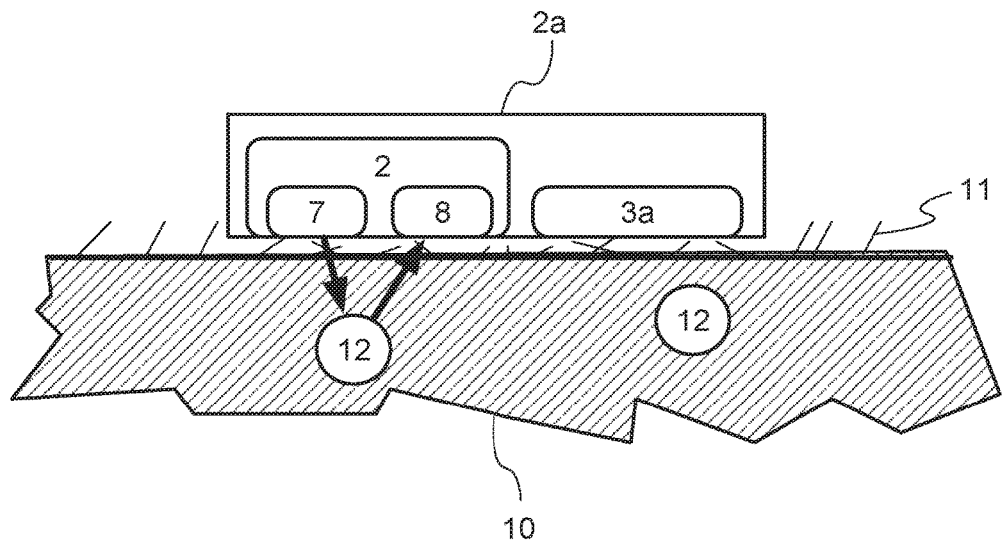
FIG. 3 schematically illustrates an individual combined sensor comprising a biometric sensor and a distance detector, according to a preferred embodiment of the present invention.

FIG. 3 illustrates a preferred first embodiment of an individual combined sensor 2a comprising an individual biometric sensor being part of the biometric sensor system 2 and distance detector 3a. The biometric sensor comprises a radiation source 7 and radiation sensor 8 arranged next to each other at the contact surface, such that they can emit light into the vicinity of the contact surface respectively receive light therefrom. Particularly, the radiation source 7 is configured to emit visible or infrared light from the contact surface towards a user's body 10, when the wearable biometric device 1 is worn by the user. In FIG. 3, the light is indicated by arrows. When the light is reflected at the body 10, in particular by blood in a blood vessel 12 located below the skin portion next to the contact surface, the reflected light is detected by the radiation sensor 8 and a corresponding primary signal is generated and provided to the signal processing unit 4. At the same time, the distance detector 3a is operable to detect a distance between it and the body surface below it, i.e. the skin. In particular, the distance detector 3a may also be sensitive to detecting a degree of presence of objects or substances between it and the skin, such as hair 11, dirt, sweat, water respectively humidity etc., which might impact the transmission of light between the biometric sensor and the body. The distance detector 3a is further operable to generate a secondary signal indicative of a coupling level between the combined sensor 2a and the body 10 and to provide it to the signal processing unit 4. The coupling level is based on the detected distance between the distance detector 3a and the body 10 and optionally also on the detected degree of presence of objects or substances between them.

Figure 4:
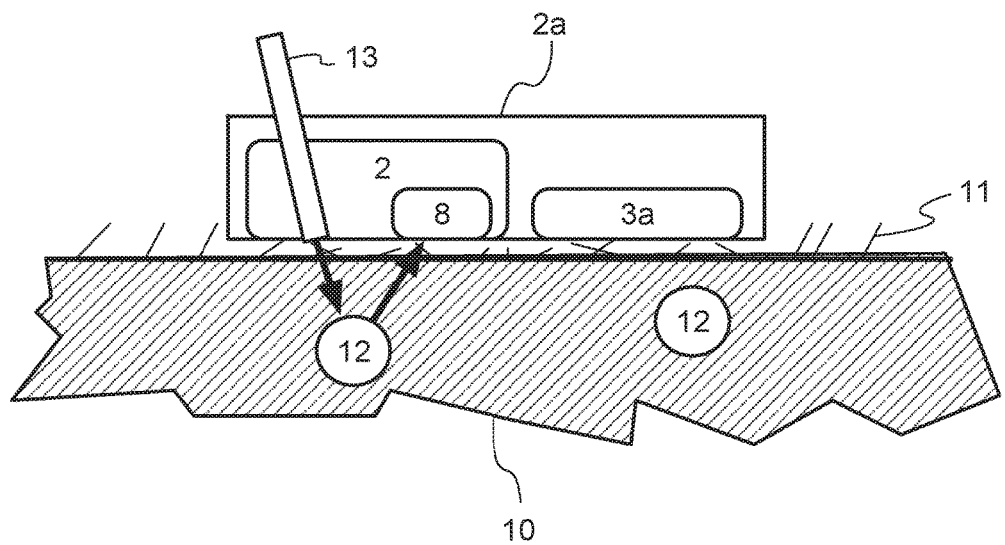
FIG. 4 schematically illustrates an individual combined sensor comprising a biometric sensor with a waveguide and a distance detector, according to another preferred embodiment of the present invention.

FIG. 4 illustrates an alternative second preferred embodiment of an individual combined sensor 2a. This combined sensor 2a is identical to the one of FIG. 3, except that instead of a radiation source 7, a waveguide 13 is provided, by which light generated at a radiation source located at another portion of the biometric sensor system 2 can be guided to the contact surface and can emit light towards the body 10. This has as an advantage that the radiation source does no longer have to be co-located with the radiation sensor 8 and the distance detector 3a. Furthermore, by using a respective plurality of waveguides, or a respective multipath waveguide, leading to various combined sensors 2a-2i, the number of radiation sources 7 can be lower than the number of combined sensors 2a-2i that are supplied with light by those radiation sources 7. In particular, a single radiation source may supply light to a plurality of combined sensors 2a-2i. This also holds true for other embodiments, where no combined sensors are used, but instead the individual biometric sensors of the biometric sensor system 2 and the individual detectors of the detector system 3 are formed separately.

Figure 5:
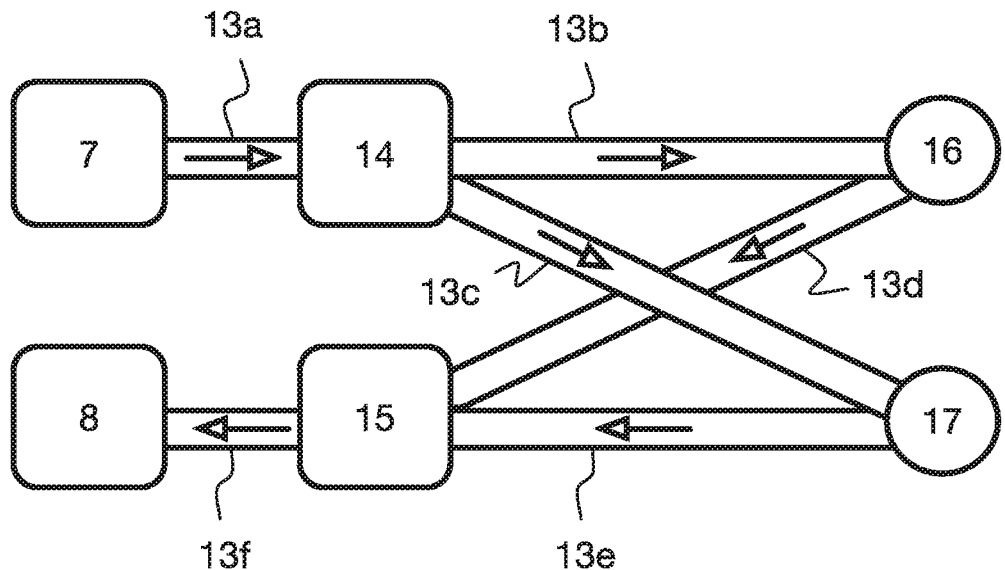
FIG. 5 schematically illustrates a preferred variant of the biometric sensor system with a radiation source, waveguides, an optical switch, a shutter system and a radiation sensor, according to another preferred embodiment of the present invention.

FIG. 5 schematically illustrates a preferred embodiment of the biometric sensor system 1, where a single radiation source 7 and a single radiation sensor 8 are used, while the number of locations 16 and 17, where measurements are taken, is greater than one, in the particular simplified example of FIG. 5 equal to 2. The radiation source 7 is configured to emit light in the visible or infrared spectrum into a waveguide 13a, which may be preferably formed as a fiber of glass or plastic material being transparent to the radiation. Waveguide 13a connects the radiation source 7 to an optical switch 14, which is adapted to selectively direct the received radiation into one or more further waveguides 13b and 13c leading to different locations 16 and 17 at the contact surface 5a, 5b of the wearable biometric device 1 (these further waveguides 13b and 13c correspond to waveguide 13 in FIG. 4). In addition, further waveguides 13d and 13e are arranged to provide a light path back from the locations 16 respectively 17 to a shutter system 15. A further waveguide 13f connects the shutter system 15 and the radiation sensor 8.

Thus, the optical switch 14 may be used to serially scan various locations 16 and 17, such that the light coming from the radiation source 7 is guided to the various locations 16 and 17 one after the other, preferably periodically, like in a time division multiplex system. According to an alternative preferred variant, the switch may also be operable to split the received light beam and direct the resulting split beams simultaneously to multiple waveguides 13b, 13c leading to all or a subset of the various locations. The shutter system 15 can be used to selectively block reflected light coming from the locations 16 and 17 that reaches the shutter system 15 through the waveguides 13d and 13e. In particular, the selective blocking of reflected light at the shutter system 15 can be controlled based on the secondary signals associated with the respective locations, such that light coming from locations whose associated secondary signal indicates a low level of coupling, is blocked, while light coming from locations whose associated secondary signal indicates a sufficiently high level of coupling (compared to a predetermined threshold level related to a minimum coupling level that is necessary in order to perform a meaningful measurement at the locations) is passed through the shutter system 15 and waveguide 13f to the light sensor 8. Alternatively, or in combination, the optical switch 14 can be controlled by the secondary signals, such that the light received by the optical switch 14 through waveguide 13c is only selectively guided to those locations 16 respectively 17 whose associated secondary signal indicates a sufficiently high level of coupling. In this way, the number of radiation sources and radiation sensors can be kept lower than the number of locations or even limited to one each, and accordingly related size and cost requirements can be kept low, while via the arrangement of the specific waveguides 13b to 13e a plurality of locations 16, 17 can be defined for taking measurements at the human body 10.

Figure 6:
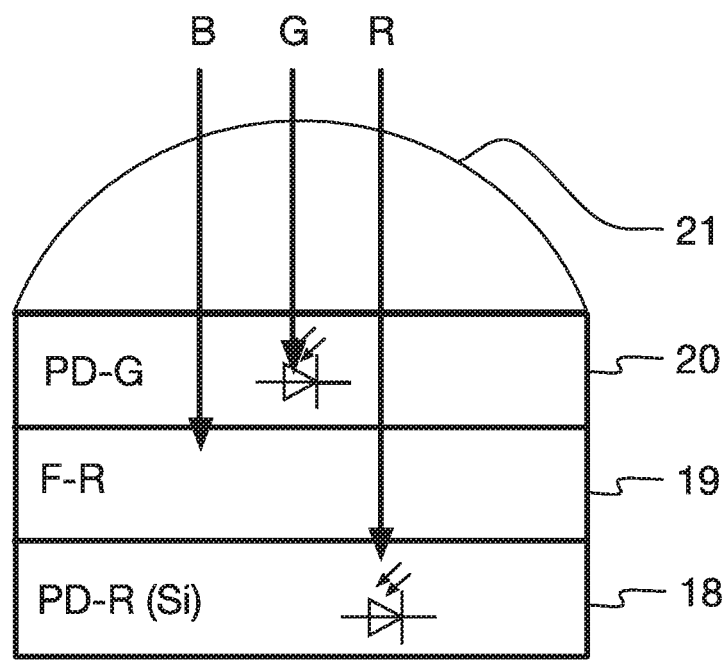
FIG. 6 schematically illustrates a radiation sensor comprising a stack of two organic photodiodes and a Si-based photodiode, according to according to preferred embodiments of the present invention.

FIG. 6 schematically illustrates an exemplary radiation sensor of the biometric sensor system, according to a preferred embodiment of the present invention. The radiation sensor comprises a stack of multiple layers. A bottom layer 18, which may be particularly formed from a Silicon (Si)-substrate, comprises one or more photodiodes (PD). On top of the bottom layer 18 a second layer 19 is formed that acts as an optical filter with a pass band for wavelengths the photodiodes in the bottom layer can detect. A third layer 20 formed on top of the second layer comprises one or more organic photodiodes and is generally transparent to light of various wavelengths, in particular to wavelengths to which its organic photodiodes only have a low or no sensitivity. Optionally, an optical lens 21 may be arranged on top of the third layer for the purpose of focusing incoming light onto the light sensitive areas of the stack, i.e. areas containing its photo diodes. For illustration only, a simple example is shown in FIG. 6, where the incoming light contains a blue component B, a green component G and a red component R. After passing the lens 21 all three components reach the third layer 20, which contains organic photodiodes PD-G being sensitive to green light. Thus the component G is at least partially absorbed and detected by the organic photodiodes of the third layer 20, while components B and R can pass on to the second layer 19. Layer 19 is a red filter F-R, i.e. it has a pass band in the red part of the spectrum, while it filters out other colors. Accordingly, components B and G (i.e. the remainder thereof) are filtered out in layer 19 and only component R can pass on to the bottom layer 18, where it is sensed by the Si-photodiodes PD-R. In summary, within the same sensor footprint, two different wavelength components that may relate to different physiological properties of the user's body—which may be in particular different blood components—may be measured at the same time. Further layers comprising organic photodiodes and/or filters may be added to the stack to provide for an even more selective sensing of different radiation components.

Figure 7:
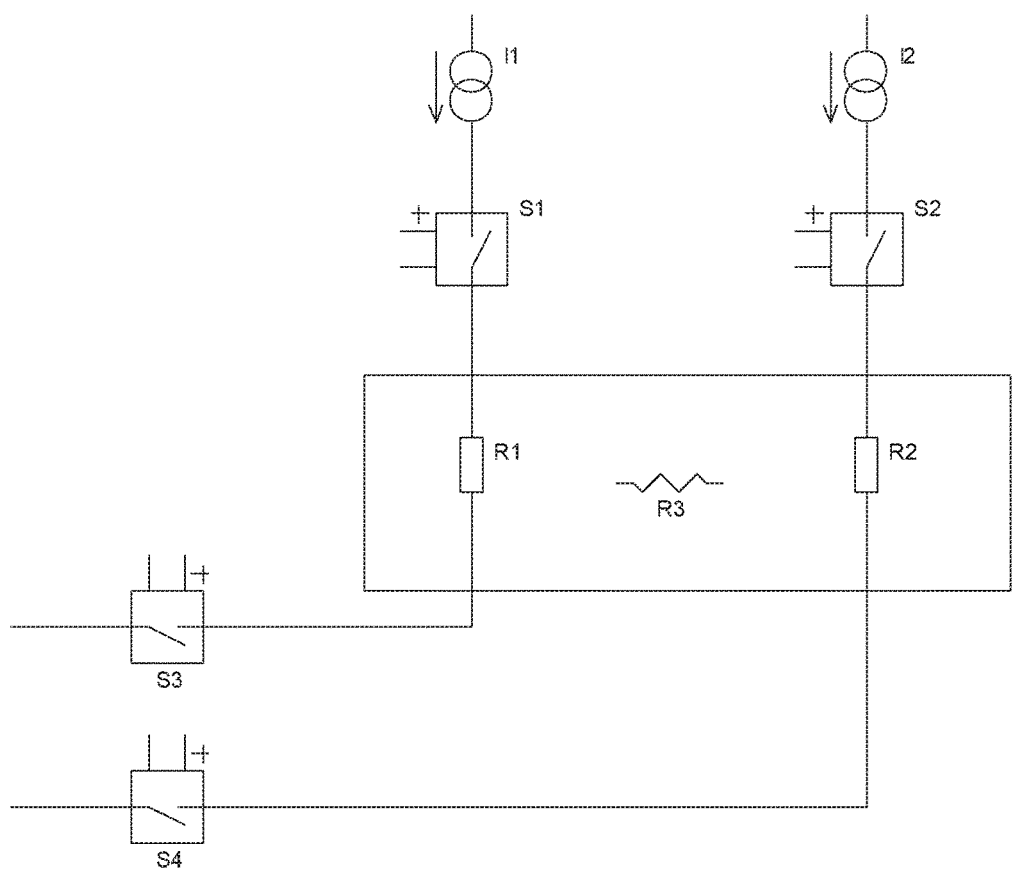
FIG. 7 illustrates a circuit diagram for an arrangement of sensors operable to measure both distance and a physiological property of a user's body, particularly humidity, according to another preferred embodiment of the present invention.

FIG. 7 illustrates a circuit diagram for an arrangement of sensors of the wearable biometric device, according to another preferred embodiment of the present invention. The arrangement comprises at least two electrical temperature-sensitive resistors R1 and R2, which are arranged on a contact surface 5a, 5b, which is configured to get in contact with the user's body when the wearable biometric devices is worn by a user (cf. FIG. 2). Each of the resistors corresponds and defines a location for measuring a level of coupling between the wearable biometric device to the body 10 of a user. The resistors R1 and R2 are each connectable via a respective switch S1 or S2 to a respective current source I1 or I2. In particular, the resistors R1 and R2 can be ohmic resistors, transistors, or any other component showing an electric resistance, at least in one mode of operation, or any mix thereof. Each of the resistors R1 and R2 can also be formed from multiple individual resistor elements, and there may be more than two resistors, while the present example only shows two (R1, R2). Further switches S3 and S4 are provided by which the respective electrical circuit through resistor R1 respectively R2 can be closed or opened.

In a first mode of operation, detector system 3 is operable to cause a temporary flow of current, such as a current pulse with a predetermined amperage and length, through resistor R1 or resistor R2 or both, by closing the respective switches S1 and S3 for R1, respectively S2 and S4 for R2. Because the resistors R1 and R2 are temperature-sensitive, their resistance depends on the temperature, which in turn is affected by the degree of coupling of the respective resistor to the body 10. In other words, when a resistor R1, R2 is having a high level of coupling to the body 10, the heat generated in the resistor R1, R2, when the current pulse flows through it, is at least partially dissipated through the body 10. Thus, in this case the temperature rise of the resistor R1, R2 is less than what it would be, if the respective resistor was not coupled to the body and fully surrounded by air (which is a very good thermal isolator). Accordingly, the temperature-dependent resistance of the respective resistor R1, R2 and therefore also a voltage drop across the respective transistor depends on the level of coupling of that resistor to the body 10. The voltage drop can then be transformed by the detector system into a respective secondary signal indicating the current level of coupling of the respective resistor R1 or R2 to the body 10.

In a second mode of operation, however, the biometric sensor system 2 is operable to apply a voltage between the first resistor R1 and the second resistor R2. In particular, this is achieved when switches S1 and S4 are closed and switches S2 and S3 are open. Then a current can flow from current source I1 through switch S1 to resistor R1 and across a resistance R3 formed by the body, specifically on its skin, to resistor R2 and through switch S4. In the alternative, switches S2 and S3 are closed and switches S1 and S4 are open, such that a current can flow from current source I2 through switch S2 to resistor R2 and across the resistance R3 formed by the body to resistor R1 and through switch S3. In an other alternative, S3 and S4 both are closed at the same time, such that there are two parallel current paths, e.g. if S1 is closed and S2 is open, one path from I1 through R1 and S3 and another path from I1 through R1, R3, R2 and S4.

In each case, the voltage drop across R3 is indicative of the resistance of R3, which in turn depends on one or more physiological parameters of the skin between R1 and R3, such as its humidity. The voltage drop across R3 can then be transformed by the biometric sensor system into a respective primary signal indicating the physiological property at the location of R1 or R2 or both. It is also possible to assign a specific location to R3. Accordingly, this arrangement can be operated in different modes of operation to measure alternatively a level of coupling or a physiological property, particularly humidity, of a user's body.

Figure 8:
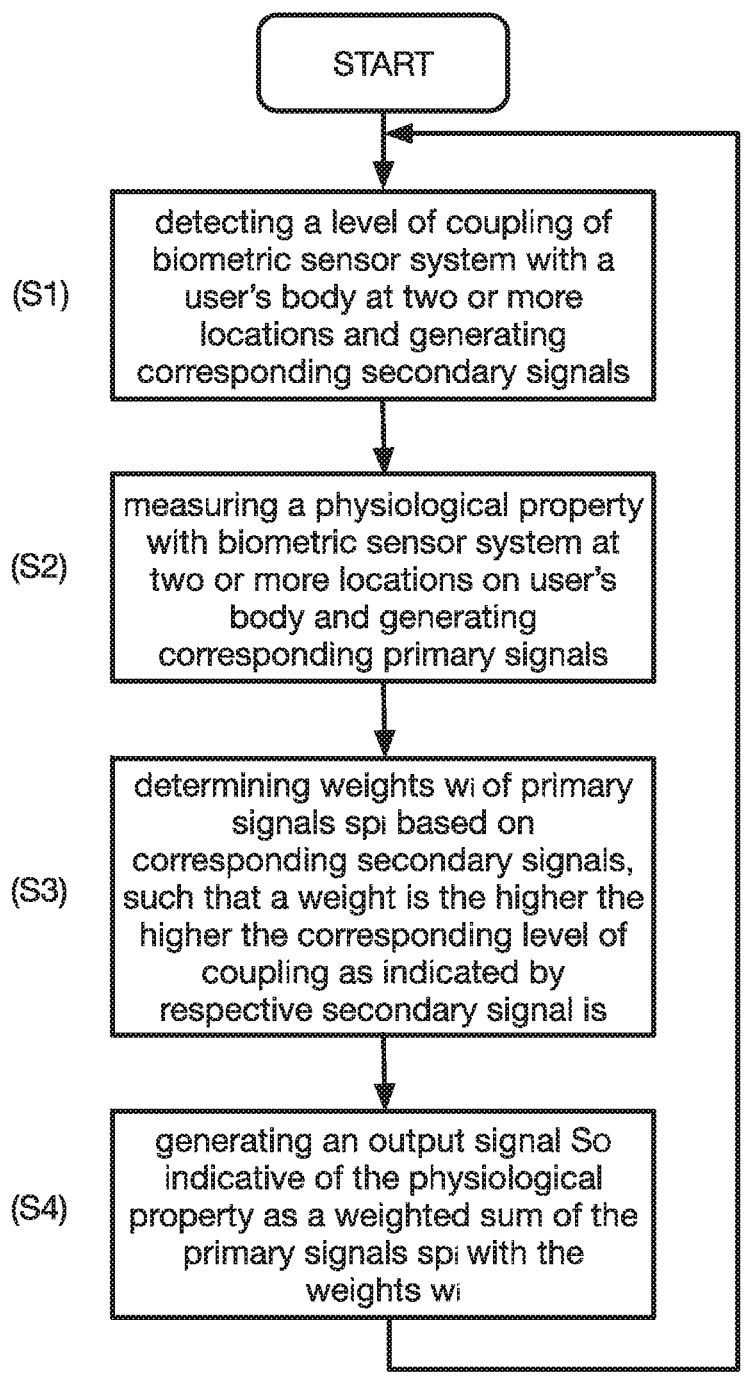
FIG. 8 illustrates a method of performing biometric measurements at a wearable biometric device, according to a preferred embodiment of the present invention.

FIG. 8 illustrates a method of performing biometric measurements at a wearable biometric device, according to a preferred embodiment of the present invention. In particular, the wearable biometric device may be a device as illustrated in FIG. 1 or 2, specifically it may be designed also according any one or more of the embodiments described in connection with FIGS. 3 to 7. The device 1 comprises a biometric sensor system 2, a detector system 3, and a signal processing unit 4, as described above.

The method comprises a first step S1 of detecting, with the detector system 3, the level of coupling of the biometric sensor system 2 with a body 10 of the user at two or more locations, when the device 1 is worn by the user. Furthermore, a secondary signal is generated per location, the secondary signal being indicative of the detected level of coupling at the respective location. The method further comprises a second step S2 of measuring, by the biometric sensor system, a physiological property at the two or more locations and of generating per location a corresponding primary signal indicative of the physiological property measured at the respective location. The second step may be performed before, after or at the same time as the first step. According to a preferred variant of the method, as illustrated in FIG. 8, it is performed after the first step. This allows for omitting measurements at such locations, where the previously detected level of coupling, as indicated by the respective primary signal, is below a threshold that is defined as a minimum level necessary for performing meaningful measurements of said physiological property. Accordingly, step S2 is then performed for a subset of N locations yielding N primary signals, while the total number M of locations, at which in principle the biometric sensor system is able to measure said physiological property may be higher (M>N). The method further comprises a third step S3 determining weights $w_i$ associated with the respective $i^{th}$ one of the N primary signals $sp_i$, with i=1, . . . , N, based on corresponding secondary signals. Thereby, a weight $w_i$ is the higher, the higher the corresponding level of coupling is, as indicated by the respective secondary signal. Accordingly, to each primary signal generated during the second step an associated weight $w_i$ is determined and primary signals $sp_i$ having a corresponding higher level of coupling receive a greater weight than primary signals having a lower corresponding level of coupling. Alternatively, the weight determination step S3 may also be performed before or at the same time as the measuring step S2.

The method further comprises a fourth step S4, were an output signal $S_O$ indicative of the physiological property is generated as a weighted sum of the primary signals $sp_i$ with the respective weights $w_i$. In particular, this weighted sum can be formed as a weighted average, i.e. as follows:

$$S_O = \frac{\sum_{i=1}^{N} w_i \cdot Sp_i}{\sum_{i=1}^{N} w_i}$$

After step S4, the process may be repeated by returning to step S1, thus enabling a continuous measurement over time.

While above at least one exemplary embodiment of the present invention has been described, it has to be noted that a great number of variation thereto exists. Furthermore, it is appreciated that the described exemplary embodiments only illustrate non-limiting examples of how the present invention can be implemented and that it is not intended to limit the scope, the application or the configuration of the herein-described apparatus' and methods. Rather, the preceding description will provide the person skilled in the art with constructions for implementing at least one exemplary embodiment of the invention, wherein it has to be understood that various changes of functionality and the arrangement of the elements of the exemplary embodiment can be made, without deviating from the subject-matter defined by the appended claims and their legal equivalents.

LIST OF REFERENCE SIGNS 1 wearable biometric device
2 biometric sensor system
2a-i combined sensors
3 detector system
3a distance detector
4 signal processing unit
5a-b portions of contact surface
6 housing
6a bracelet
7 radiation source of biometric sensor system
8 radiation sensor of biometric sensor system
9 distance sensor of detector system
10 body of user
11 hair
12 blood vessels
13 waveguide
13a-f waveguides
14 optical switch
15 shutter system
16 first location
17 second location
18 bottom layer (esp. Si-substrate with photodiodes) of radiation sensor
19 second layer (esp. filter) of radiation sensor
20 third layer (with organic photo diodes) of radiation sensor
R1, R2 temperature-sensitive resistors
R3 resistance of current path across body
S1-S4 electrical switches
I1, I2 current sources

The invention claimed is:

1. Wearable biometric device, comprising:
   a biometric sensor system adapted to measure a physiological property of a user's body in relation to two or more different locations at the body surface and to provide for each such location an associated primary signal indicative of said measured physiological property;
   a detector system adapted to detect a level of coupling of the biometric sensor system with the body at each of the locations and to provide for each of the locations an associated secondary signal indicative of said detected level of coupling;
   a signal processing unit adapted to receive the primary signals and the associated secondary signals and to generate an output signal indicative of said physiological property as a function of the received primary and secondary signals, such that the output signal's functional dependency on a first one of the primary signals is less than its functional dependency on a second one of the primary signals, if the secondary signal associated with the first one of the primary signals indicates a lower coupling level than the secondary signal associated with the second one of the primary signals.

2. The wearable biometric device of claim 1, wherein:
   in an active mode an energy consumption of the detector system per location is lower than that of the biometric sensor system; and
   the signal processing unit is further adapted to selectively activate the biometric sensor system such that the generation of a respective primary signal is activated only for one of the locations having a coupling level, as indicated by the associated secondary signals, above a defined threshold.

3. The wearable biometric device of claim 2, wherein the signal processing unit is further configured to initiate a transition of the biometric sensor system into a low power mode, when for a predetermined duration no secondary signals indicating a sufficiently good level of coupling have been received.

4. The wearable biometric device of claim 1, wherein the biometric sensor system is operable in different modes of operation including a first mode in which it is configured to provide said primary signals, and a second mode, in which it is configured to provide at least a subset of said associated secondary signals.

5. The wearable biometric device of claim 1, wherein the signal processing unit is further adapted to selectively receive the primary signals, the secondary signals, or both as a function of time or the locations or both as a function of time and the locations.

6. The wearable biometric device of claim 1, wherein said function to be used by the signal processing unit for generating the output signal involves forming a weighted sum of the received primary signals, wherein the weight of a first one of the primary signals is smaller than the weight of a second one of the primary signals, if the secondary signal associated with the first one of the primary signals indicates a lower coupling level than the secondary signal associated with the second one of the primary signals.

7. The wearable biometric device of claim 1, wherein the detector system comprises one or more distance sensors configured to measure the respective distances between each of at least two of said locations at the user's body and the biometric sensor system.

8. The wearable biometric device of claim 7, wherein the detector system further comprises:
   at least one light source adapted to emit a predetermined calibration light signal towards the user's body when the device is worn by the user; and
   at least one light detector adapted to receive the light signal after it has been reflected at a location on the user's body and to generate a secondary signal corresponding to the level of coupling at the location based on a comparison of the received reflected signal with the predetermined calibration signal.

9. The wearable biometric device of claim 7, wherein the biometric sensor system comprises:
   at least one radiation source arranged to emit electromagnetic radiation, at least partially, onto one or more of said locations at the user's body when the biometric device is worn by the user; and
   at least one corresponding radiation sensor adapted to receive said radiation, at least partially, after it has passed through or has been reflected by the body;
   wherein the biometric sensor system comprises one or more waveguides for directing the radiation from the at least one radiation source to one or more of the locations or from the one or more locations to the at least one corresponding radiation sensors or wherein the one or more waveguides are configured for directing the radiation from the at least one radiation source to one or more of the locations and from the one or more locations to the at least one corresponding radiation source sensor.

10. The wearable biometric device of claim 9, wherein the biometric sensor system further comprises an optical switch adapted to selectively direct radiation emitted by the at least one radiation source to a subset of one or more of the locations.

11. The wearable biometric device of claim 10, wherein the biometric sensor system further comprises a shutter system for selectively blocking one or more radiation paths provided in the one or more waveguides, the paths connecting the one or more locations to the at least one corresponding radiation sensor.

12. The wearable biometric device of claim 9, wherein the at least one radiation source is adapted to selectively emit radiation in different predetermined wavelengths or wavelength ranges that are aligned with the spectral responses of corresponding different chemical substances to be detected within the user's body.

13. The wearable biometric device of claim 1, wherein the biometric sensor system comprises:
at least one radiation source arranged to emit electromagnetic radiation, at least partially, onto one or more of said locations at the user's body when the biometric device is worn by the user;
at least one corresponding radiation sensor to receive said radiation, at least partially, after it has passed through or has been reflected by the body; and
a filter arrangement comprising one or more radiation filters arranged between one or more of the radiation sources on the one hand and corresponding one or more of the radiation sensors on the other hand, the filter arrangement being configured to selectively let pass radiation in one or more passing band regions of the wavelength spectrum emitted by the one or more radiation sources, wherein the passing band regions correspond to wavelength ranges of the spectral responses of preselected chemical substances to be detected.

14. The wearable biometric device of claim 1, wherein the biometric sensor system comprises:
at least one radiation source arranged to emit electromagnetic radiation, at least partially, onto one or more of said locations at the user's body when the biometric device is worn by the user;
at least one corresponding radiation sensor to receive said radiation, at least partially, after it has passed through or has been reflected by the body;
wherein:
at least one of the radiation sensors comprises two or more photodiodes arranged in different layers of a stack, the stack having a top face configured to receive radiation to be detected, each photodiode having one or more specific sensitivity wavelength ranges in which it can detect radiation;
one or more of the photodiodes are organic photo diodes being at least partially transparent to radiation having a wavelength outside of their respective one or more sensitivity wavelength ranges; and
a first one of the one or more organic photodiodes is arranged in a first layer positioned closer to the top face of the stack than a second layer comprising a second one of the photodiodes such that at least a portion of incoming radiation to be detected first reaches the first organic photo diode before reaching the second photodiode.

15. The wearable biometric device of claim 1, wherein the biometric sensor system comprises a sensor selected from the group consisting of an oximeter, a temperature sensor, a humidity sensor, an accelerometer, and a radiation sensor.

16. The wearable biometric device of claim 15, further comprising:
a first resistor arranged at a first position on a contact surface of the wearable biometric device, the contact surface being configured to get in contact with the user's body surface at a first location corresponding to the first position, when the wearable biometric device is worn by a user;
wherein the detector system is operable to:
cause a temporary flow of current through the first resistor that results in a temperature increase at the first resistor;
to determine a level of coupling of the biometric sensor system with the body based on a physical quantity affected by a change of the resistance of the first resistor caused by the temperature increase; and
to provide an associated secondary signal indicative of said detected level of coupling.

17. The wearable biometric device of claim 16, further comprising:
a second resistor arranged on the contact surface of the wearable biometric device at a second position being different from the first position, the contact surface being further configured to get in contact with the user's body surface at a second location corresponding to the second position, when the wearable biometric device is worn by a user;
wherein the biometric sensor system is operable to:
apply a voltage between the first resistor and the second resistor;
measure a physiological property of the body that affects the resistance of a current path forming between the first location and the second location across the body when both the first resistor and the second resistor are in contact with the body and the voltage is applied between the first resistor and the second resistor by measuring a physical quantity depending on said resistance of the current path; and
to provide a primary signal associated with the first location or the second location that is derived from the measured quantity.

18. The wearable biometric device of claim 1, wherein:
the biometric sensor system, the detector system or both are structured as a fixed array of individual sensors; and
the signal processing unit is further adapted to:
derive from the primary or secondary signals or both on the one hand and the positions of the sensors respectively detectors in the array on the other hand a position of the biometric device relative to the user's body by applying a pattern recognition algorithm to said signals; and
to determine said function of the received primary and secondary signals for generating the output signal based on one or more patterns on the user's body that were recognized by the application of said pattern recognition algorithm.

19. The wearable biometric device of claim 1, wherein the detector system or the signal processing unit are configured to generate a signal, if during a predetermined duration a coupling level of the biometric sensor system has been below a predetermined threshold level for all of the locations, wherein the threshold level defines a minimum level for meaningful measurements of the respective physiological property.

20. A method of performing biometric measurements at a wearable biometric device, comprising:
- measuring, with a biometric sensor system, a predetermined physiological property of a user's body in relation to two or more different locations at the body and generating for each such location an associated primary signal indicative of said measured physiological property;
- detecting, with a detector system, a level of coupling of the biometric sensor system with the body at each of the locations and providing for each of the locations an associated secondary signal indicative of said detected level of coupling;
- generating, an output signal indicative of said physiological property as a function of the primary and secondary signals, such that the output signal's functional dependency on a first one of the primary signals is less than its dependency on a second one of the primary signals, if the secondary signal associated with the first one of the primary signals indicates a lower coupling level than the secondary signal associated with the second one of the primary signals.

* * * * *